US012508341B2

(12) United States Patent
Kryukov et al.

(10) Patent No.: US 12,508,341 B2
(45) Date of Patent: Dec. 30, 2025

(54) PERSONAL AND MOBILE DEVICES FOR PROVIDING BIOLOGICAL PROTECTION BY THE ULTRAVIOLET IRRADIATION OF RECIRCULATED AIR

(71) Applicant: LIMITED LIABILITY COMPANY "SIZAR", Moscow (RU)

(72) Inventors: Valeriy Vladimirovich Kryukov, Moscow (RU); Evgeniy Mikhailovich Stelmakhovich, g. Scherbinka (RU)

(73) Assignee: LIMITED LIABILITY COMPANY "SIZAR", Moscow (RU)

(*) Notice: Subject to any disclaimer, the term of this patent is extended or adjusted under 35 U.S.C. 154(b) by 507 days.

(21) Appl. No.: 17/928,559

(22) PCT Filed: May 28, 2021

(86) PCT No.: PCT/RU2021/050149
§ 371 (c)(1),
(2) Date: Nov. 29, 2022

(87) PCT Pub. No.: WO2021/242148
PCT Pub. Date: Dec. 2, 2021

(65) Prior Publication Data
US 2023/0248877 A1 Aug. 10, 2023

(30) Foreign Application Priority Data
May 29, 2020 (RU) ........................... RU2020117832

(51) Int. Cl.
*A61L 9/20* (2006.01)
*A62B 18/00* (2006.01)
(Continued)

(52) U.S. Cl.
CPC .............. *A61L 9/20* (2013.01); *A62B 18/006* (2013.01); *A62B 18/10* (2013.01); *A62B 23/02* (2013.01);
(Continued)

(58) Field of Classification Search
CPC .......................................................... A61L 9/20
See application file for complete search history.

(56) References Cited

U.S. PATENT DOCUMENTS

| | | | |
|---|---|---|---|
| 5,165,395 | A | 11/1992 | Ricci |
| 2014/0360496 | A1 | 12/2014 | Reese |

(Continued)

FOREIGN PATENT DOCUMENTS

| | | |
|---|---|---|
| CN | 206587294 | 10/2017 |
| RU | 2 404 816 | 11/2010 |

OTHER PUBLICATIONS

International Search Report for PCT/RU2021/050149 dated Oct. 7, 2021, 2 pages.

(Continued)

*Primary Examiner* — Kevin Joyner
(74) *Attorney, Agent, or Firm* — Nixon & Vanderhye PC

(57) ABSTRACT

The invention can be used to produce personal protection systems of respiratory organs (RPE) and organs of vision from airborne and aerosol pathogens. Additionally, it can be used to create mobile low-power closed-type recirculation systems of UV cleaning and air disinfection in small rooms and volumes: salons and cabins of various vehicles, offices, classrooms, medical rooms, etc. According to the claimed characteristics, the invention provides a high level of bactericidal treatment of air flows, including human breathing, by irradiating the flow with UV radiation from UVC-LED source with the formation of multiple times amplified luminous flux in the multi-pass irradiation chamber. The tech-
(Continued)

Figure 1:
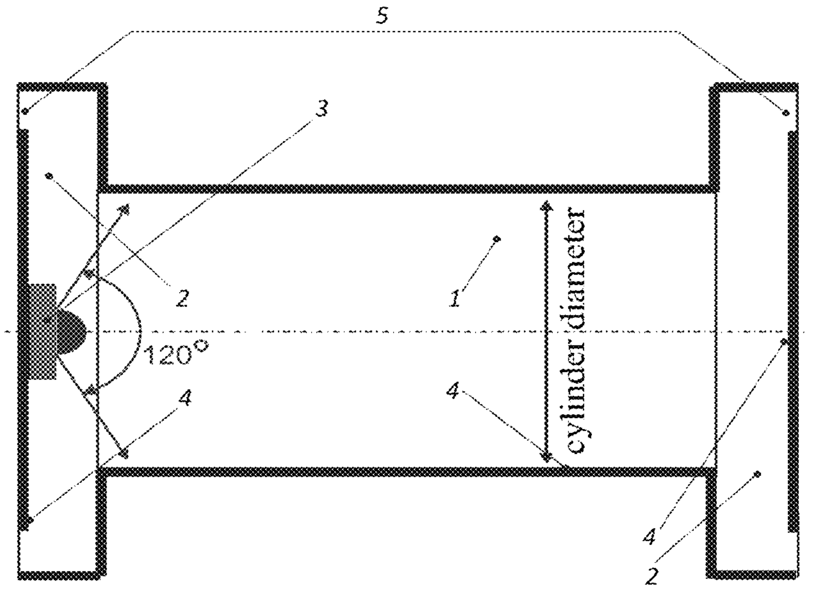

nical result is expressed in a multiple increase in the bactericidal efficacy of the device compared to devices without such a chamber, as well as in the same reduction in the requirements for the radiation power of the primary radiators according to the required bactericidal efficacy of the device.

17 Claims, 3 Drawing Sheets

(51) Int. Cl.
*A62B 18/10* (2006.01)
*A62B 23/02* (2006.01)

(52) U.S. Cl.
CPC ....... *A61L 2209/12* (2013.01); *A61L 2209/14* (2013.01)

(56) References Cited

U.S. PATENT DOCUMENTS

2016/0001108 A1 1/2016 Zhou et al.
2021/0330853 A1 * 10/2021 Mizandari ................ A62B 7/10

OTHER PUBLICATIONS

Written Opinion of the ISA for PCT/RU2021/050149 dated Oct. 7, 2021, 4 pages.

* cited by examiner

PERSONAL AND MOBILE DEVICES FOR PROVIDING BIOLOGICAL PROTECTION BY THE ULTRAVIOLET IRRADIATION OF RECIRCULATED AIR

This application is the U.S. national phase of International Application No. PCT/RU2021/050149 filed May 28, 2021 which designated the U.S. and claims priority to RU 2020117832 filed May 29, 2020, the entire contents of each of which are hereby incorporated by reference.

The invention can be used to create mobile air recirculators and personal protective equipment for the respiratory organs (RPE) and organs of vision against ingress into their mucous membranes by pathogenic organisms, primarily viruses, that spread by air and aerosols.

Over the past 20 years, there have been several significant outbreaks of viral diseases with varying degrees of virion aggressiveness, including the COVID-19 pandemic. The most dangerous diseases are those carried by droplet and airborne (aerosol) transmission, as well as through contact with the mucous membrane of the airway and eyes: about 10% of patients are infected through the mucous membranes of the eyes, 90% —through the respiratory organs. The methods and means of disinfection and treatment of premises/objects used in this case are widely known, and involve ozonation, disinfection treatment with chemical compounds or UV irradiation (ultraviolet germicidal irradiation).

In research papers [1, 2], the authors evaluated the effectiveness of harsh bactericidal ultraviolet on viral aerosols by considering viruses with different types of nucleic acids at different relative humidity during exposure to ultraviolet. For airborne viruses, the ultraviolet dose for 90% inactivation was: 339-423 $\mu W \times s/cm^2$ for single-stranded RNA, 444-494 $\mu W \times s/cm^2$ for single-stranded DNA, 662-863 $\mu W \times s/cm^2$ for double-stranded RNA and 910-1196 $\mu W \times s/cm^2$ for double-stranded DNA.

It is noteworthy that for the tested classes of viruses, it took twice as much ultraviolet radiation to achieve 99% inactivation as was needed to achieve 90% inactivation. In addition, it was found that airborne viruses with single-stranded nucleic acid are more susceptible to ultraviolet inactivation than with double-stranded RNA and DNA. For all tested viruses with the same degree of inactivation, the dose of ultraviolet radiation at a relative humidity of 85% was higher than at a relative humidity of 55%. The reason is that the water sorption on the surface of the virus provides protection against UV-induced damage to DNA or RNA. For example, COVID-19, "Wuhan pneumonia", contains single-stranded RNA, which corresponds to an irradiation dose of 339-423 $\mu W \times s/cm^2$ ultraviolet with a wavelength of 254 nm (90% air disinfection). Therefore, 700-850 $\mu W \times s/cm^2$ provide 99% disinfection, and 1400-1700 $\mu W \times s/cm^2$ already provide 99.9% disinfection according to COVID-19.

Based on existing data on the UV radiation effects on various viruses and other pathogens, mercury lamps have been created and used for irradiating premises and disinfecting medical and household appliances and products for a long time. With the advent of new generation lamps and UVC (ultraviolet) LEDs, the range of radiation disinfection devices has expanded significantly. Were invented flow-through (recirculating) devices capable of disinfecting the air in the premises at the time when people were in. Moreover, have been created recirculating UV water sterilizers.

However, recirculators with UV irradiation, ozonators and antiseptic sprays are ineffective against airborne forms of infection in large rooms with significant infiltration and high density of people flow (personal and public transport, shops, cinemas, cafes, public areas, etc.). Furthermore, hazmat suits with self-contained breathing apparatus and gas masks are extremely inconvenient and inaccessible to the absolute majority of the population and workers of enterprises. Moreover, according to many experts, masks, including the respiratory type, class FFP-3(N-95) are effective only in cases when the infection from the infected person comes out concentrated with fine sputum. In addition, with constant breathing, moisture with dissolved microbes diffuses deep into the mask and eventually enters the body with inhaled air.

The creation of UVC LEDs with wavelengths close to the spectrum of mercury and other discharge UV lamps, in conjunction with their small dimensions and energy consumption (low-voltage direct current from 6 V) entailed the development of all kinds of RPE circuits with built-in emitters that increase the effectiveness of protection against viral infections. Examples of such designs can be masks in which the UV emitter is placed directly in the breathing area [3] or in a device connected to this mask by a nozzle [4]. However, despite the impressive number of inventions, utility models and various designs of RPE devices with UV emitters, at the moment there is no use of them anywhere in the world. The reason for the lack of implemented inventions of this kind lies in the calculation of UV irradiation effectiveness of contaminated air in small flow-through chambers.

Analysis of engineering methods for calculating the required power of the emitters revealed a number of obvious "inconsistencies". Data on exposure surface doses of $H_s$ for $\lambda \approx 254$ nm in engineering tables [5] for some virions (for example: Hepatitis virus, Influenza virus) regarding the bactericidal efficacy J6K gave serious discrepancies with data on single-stranded RNA viruses from the researches [1, 2]. At the same time, the tables, as stated in the publication, are experimental and real working products are designed and implemented on their basis.

The second serious discrepancy, already inside the engineering tables [5], was the determination of surface $H_s$ and volumetric $H_v$ doses as constants from a specific microorganism, UV wavelength and a given J6K.

These "inconsistencies" or features of the calculation methodology were leveled by the experimental "bactericidal flow utilization coefficient" and "room index".

It is necessary to explain that the experiment to determine doses can be full-scale or laboratory-scale. Nonetheless, it passes with the irradiation of a specific type of emitters of a certain specific volume or surface infected with specific airborne microorganisms. Important factors for calculating radiation doses are the volume shape, the type and angle of the emitters location, the characteristics of the photon flux (spatial and angular distribution, frequency spectrum). The role of the object's shape is almost decisive. If we place a point source in a long corridor or in a cube-shaped office, it would be comparable with using a ball or a long cylinder the same volume of both as a flask. Thus, matching $H_s$ and $H_v$ of different objects with the same volume will be incorrect due to the spatial distribution influence of the source radiation on its intensity from a distance. The same can be said with certainty about the source type. The discharge lamp and the diode have completely different radiation distribution. Therefore, correlating their brightness or power in different angles would be inaccurate. In other words, it is possible to use $H_s$ and $H_v$ as related constants in calculations only if the shape of the irradiated object and the type of emitter are similar. Since there are no comments on the engineering tables [5] regarding the method of their experimental verification, the authors of this solution used in further calculations the data of research papers [1, 2], in which the mechanism of the experiment is disclosed and the data on $H_s$ can be confidently considered reasonable, while the volume dose of H., which is necessary for the evaluation of flux disinfection, is needed to extrapolate to a similar volume. Further in the text, this value is called the specific volumetric heat input of the source (J/$cm^3$).

Experimental data was published in research paper [1] and later described in the article [2]. The analysis of the experimental setup, where these results were obtained, showed the following features. Irradiation of air infected with virions was carried out from a side angle with UV lamps in a quartz glass flask (with minimal UV absorption by the walls). The diameter of the flask (cuvette) was d=5 cm and the length was about L=20 cm. The maximum cross-sectional area of the cylinder along its axis $S_{max}$=dL=100 $cm^2$. Each photon wave from the sources (lamps) passed through the cylindrical flask (cuvette) in the radial direction (normal to S) only ONCE. Thus, the total flux (photon/sec./$cm^2$) passed through the average irradiation area of the entire air mass (by cylinder volume): hL, where $h=d/2^{1/2}$. Therefore, through <S>=71 $cm^2$, provided that all photons of the flux in the infected medium have approximately equal path.

Let us pay attention to the physical model of the inactivation process. Photons flux per unit of time through the specified volume and its average cross-sectional area (1/$cm^3$ and 1/$cm^2$) is many orders of magnitude greater than the concentration of virions, as well as the events of photon absorption by virions and lesions of these virions. Thus, the absolute and overwhelming number of photons from lamps simply leaves the volume without participating in the inactivation of virions. Additionally, over time, the probability of effective virion damage decreases exponentially with a reduction in the concentration of live, unaffected virions [1, 2]. This circumstance allows us to consider the concept of “radiation dose” in the form of energy that has passed through a unit of the area averaged by the substance volume, as an objective value of the impact and a constant for determining the degree of this impact (a damage factor). Exactly this value was determined in the experiment in relation to the degree of virions inactivation from the initial concentration.

Consider one of the results. As it was experimentally established, the UV irradiation dose for inactivation of 99.9% of 1-RNA virions (similar to, for example, COVID-19) was achieved at a dose level of D=1400-1700 μW*sec/$cm^2$. Multiply the maximum amount of the received dose by the average irradiation area and divide by the irradiated volume: $E_v \approx D \times S/V \approx 300$ μJ/$cm^3$. This is the value of the required specific heat input of the emitters into the experimental flask volume.

Let us determine the specific volumetric heat input of the radiation source for disinfection (Ultraviolet Germicidal Irradiation method) of a small room 5×5×3 meters for a given pathogen, the corresponding surface dose and level of inactivation. Consider the source to be located in the center of the room so that all its radiation involved in inactivation is approximately equally probable. The absorbing surface area (absorption by objects, walls, floor and ceiling 100%) is 25×2+15×4=110 $m^2=1.1\times10^6$ $cm^2$. The volume of the room is 5×5×3=75 $m^3$-75×$10^6$ $cm^3$. Based on the meaning of the dose concept: D=W×t/S=E/S, we obtain the total radiation energy required to solve this problem: E=1870 J=Wt. The specific volumetric heat input of the source should be $E_v \approx 25$ μJ/$cm^3$.

We observe a large difference in the required specific heat input to achieve the same level of inactivation in a small experimental setup and indoors. The volume of the flask is only 400 $cm^3$, and the volume of the room is 75×$10^6$ $cm^3$. In this case, the heat input differs as 300: 25, that is, by a factor of 12 (logarithmic dependence 1n ($V_1/V_2$)=1n(75×$10^6$ $cm^3$/400 $cm^3$)≈12).

At the elementary level, this result can be easily explained by the exponential dependence of the photon hitting a living virion probability with an increase in the wave propagation volume. Thus, in a large volume, a photon travels a longer path before it is absorbed by the wall (or exits the interaction system). In a 5×5×3 meter room, its lifetime is about 10 ns, the average path length in the environment is about 3 meters. In the experimental setup flask, this is 0.1 ns and about 3 cm, respectively.

Therefore, the approximation for the parameter $E_v \approx E_v(V_0)/|1n(V/V_0)|(a)$ will be fair. It shows that linear extrapolation for correction coefficients works, more or less correctly, in the field of calculating volumes that differ by 1-2 orders of magnitude but completely does not work with a difference of 5-6 orders of magnitude, which we observe in practice as a result of the experiments under consideration [1, 2].

The parameter $E_v$ is extremely important, since it can be used to determine the required power of the radiation source for disinfecting a specific flowing volume of air. Using the obtained similarity formula and calculated from the confirmed experiment $E_v$ ($V_0$) and $V_0$, we can get the necessary power of the radiation source for the RPE relative to the dimensions of its irradiation chamber and the air flow through it. $E_v=W_\lambda \times t/V$, where $W_\lambda$ is the power of the optical field in the irradiation chamber, t is the irradiation time, V is the volume of the chamber. $E_v=W_\lambda \times t/V=W_\lambda/v$, where v=V/t is the volumetric air flow through the irradiation chamber. $W_\lambda$ is the power of the optical field in the irradiation chamber—numerically equal to the radiation power of the source passing through the volume of the chamber to the complete loss of photons (going outside the chamber, absorption).

An important conclusion from the above calculated characteristics is that with a decrease in the dimensions of the irradiation chamber, the required specific heat input increases and, hence, so does the power of the source. That is why in [3] the option with multiple diode sources was considered, in [4]—with a separate disinfection chamber. It should be noted that both of these options have significant disadvantages in combating viral infection by UV irradiation. Despite the advantages of UVB—UVC diodes over UV lamps, both applications show the high cost of a group of diodes (dozens of pieces are required), high energy consumption (large battery capacity), rather significant parasitic heat generation, large size and weight of devices. These factors can explain the lack of patented developments implementation in this area.

Thus, the authors solve the problem of creating affordable and highly effective means of personal biological protection (primarily for respiratory organs) based on point sources of UV radiation, including mobile recirculators with UV emitters for transport and small rooms with autonomous or on-board low-voltage power supply based on UVC LEDs, etc. The technical result achieved by solving this problem is to increase the level of bactericidal efficacy of respiratory protection devices and other air disinfection devices.

To achieve this result, the Device for inactivating pathogenic microorganisms in the air flow is claimed. Further—the Device, made in the form of a flow-through chamber having an internal volume and at least one wall limiting such internal volume. At least one LED of the ultraviolet radiation spectrum is located in the internal volume of the chamber, while the entire internal surface of at least one specified wall is coated or made of a material reflecting ultraviolet radiation to form a multi-pass optical system. At least two through-slits or holes are made in at least one specified wall, one of which is essentially an inlet, the second is an outlet from the condition of air flow through the inner volume of the chamber.

The device can optionally be equipped with an LED power supply, and the chamber is made of cylindrical, spherical, hemispherical, simple or complex geometric shape with the intersection of curved surfaces. In addition, the ratio of the sum of all slits or holes areas to the entire area of the inner surface of, at least, one specified chamber wall is optionally minimal from the condition of the air flow passage during inhalation/exhalation or air pumping.

To achieve the desired result, the personal respiratory protection device is also claimed. The device is made in the form of a mask covering at least the respiratory organs, with at least one airway and an attachment mounted on the mask, which is made or contains the above Device from the condition that the exit through-slit or hole of such Device faces the airway, and the entrance through-slit or hole faces the surrounding atmosphere and is covered by a breathable filter.

Optionally, an air-permeable membrane or filter can additionally be located between the mask and the exit through-slit or hole, and the entrance through-slit or hole is additionally closed by a breathing valve.

To achieve this result, an air disinfection device is claimed as well, containing means of air intake and forced air pumping, an exhaust bell mouth and the above Device. The Device entrance through-slit or hole faces to the air intake and pumping means, the exit slit or hole faces to the exhaust bell mouth.

The essence of the claimed group of inventions is explained by the following graphic materials.

Figure 2:
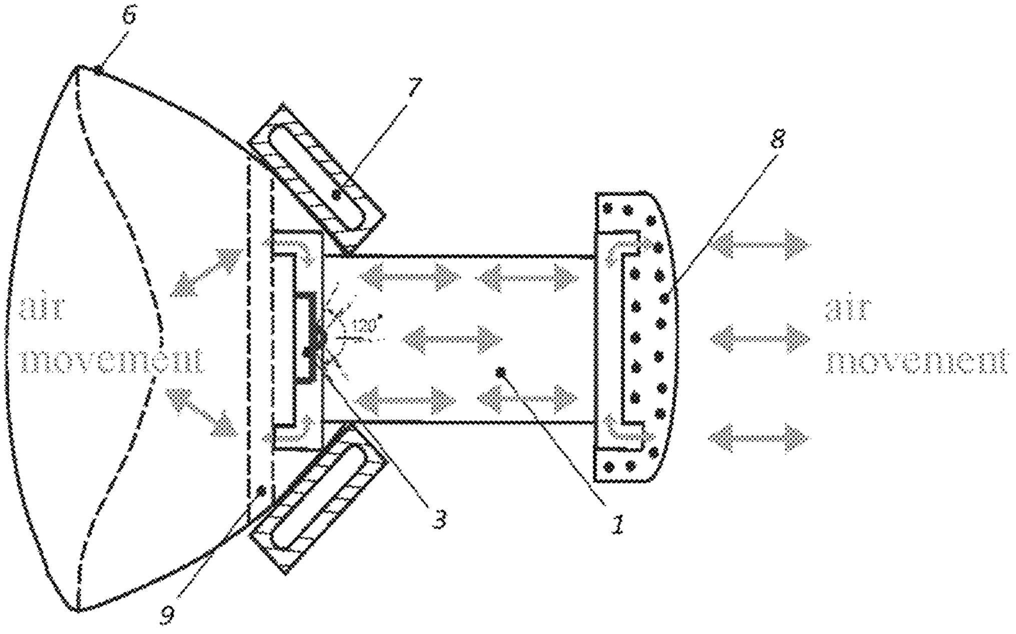
Figure 3:
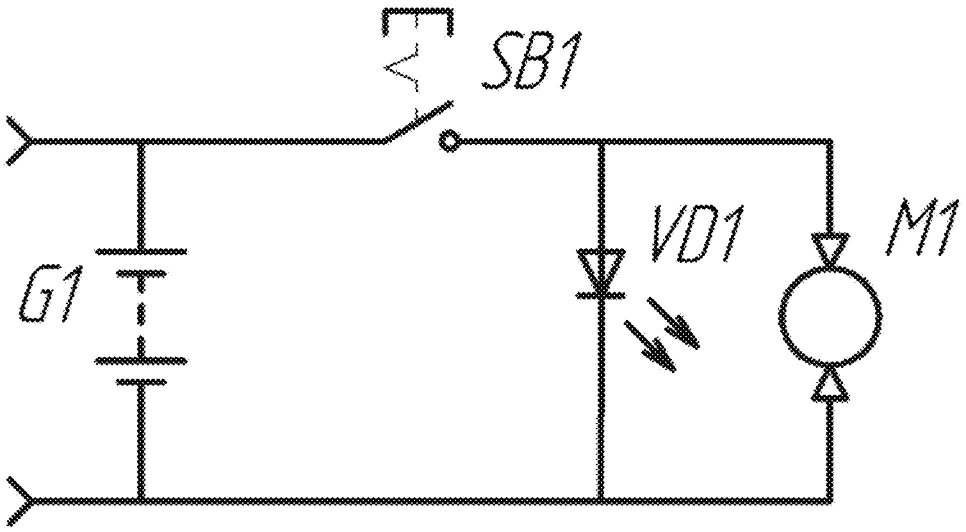
Figure 4:
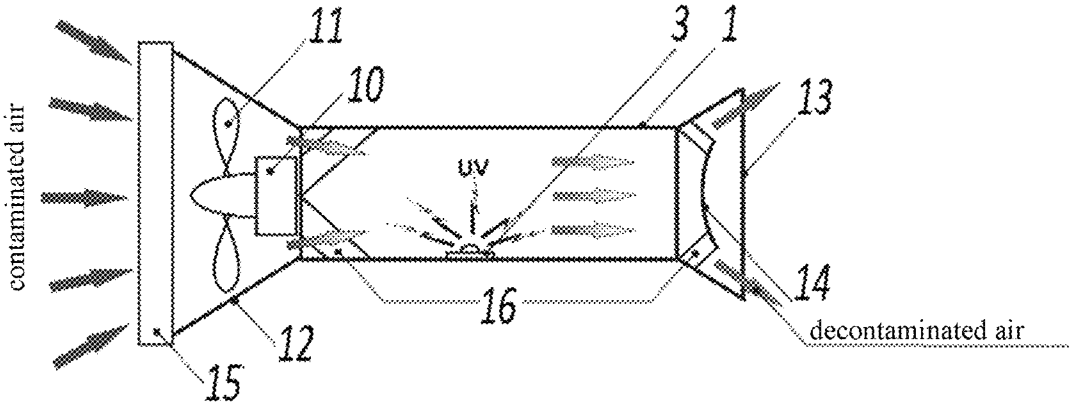
Figure 5:
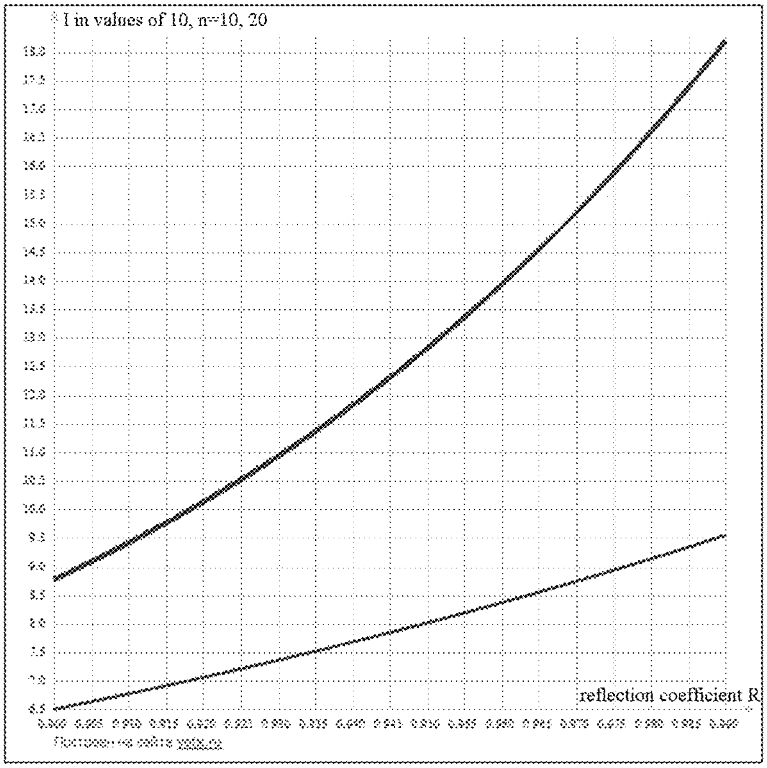

FIG. 1. shows the basic general design scheme of the claimed Device; in FIG. 2.—the basic design scheme of the personal respiratory protection equipment (RPE) based on the Device according to FIG. 1.; in FIG. 3.—the power supply scheme of the RPE; in FIG. 4.—the basic design scheme of the air disinfection (mobile) device with forced recirculation based on the Device according to FIG. 1.; FIG. 5. shows the dependence of the increase in the optical field intensity in a multi-pass irradiation chamber in units of the intensity of the original source on the reflection coefficient of the inner surfaces (average number of passes n=10, 20); in FIG. 6.—the dependence of the increase in the optical field intensity in a multi-pass irradiation chamber in units of the intensity of the original source on the average number of radiation passes (the reflection coefficient from the inner surfaces R=0.90-0.99).

The claimed group of the invention is based on the well-known principle of treating contaminated air with ultraviolet radiation with a wavelength of 200-280 nm (UVC spectrum) from existing scientific and technical practice. The fundamental difference from the existing technical solutions is the use of a multi-pass optical system (multi-pass air flow irradiation chamber) as the main unit (element) of the claimed devices. This makes it possible to obtain in the internal volume of the inactivation device chamber a repeatedly enhanced relative to the primary intensity of the optical field source, as a consequence, repeatedly reducing the requirements for the power of the ultraviolet radiation source The possibility of achieving the result, in this case, is due to the fact that the use of a multi-pass (along the optical path) irradiation chamber with an inner reflecting surface allows to attain multiple reflections of photons participating in the generation of an optical disinfecting field in the internal volume of the chamber, in which, as a consequence, the power of the optical field in the irradiation chamber $W_\lambda$will consist of a discrete series waves of different generations.

Indeed, the power of the radiation source is W=I×hv, where I is the number of photons emitted per unit of time (flux), and hv is their energy. If a photon once passes along its average path through the volume of the chamber, then the power of the optical field is equal to the power of the source. However, if photons experience n reflections on average before they are lost through air slits, then the photon flux is $I=I_0+I_0R+I_0R^2+ \ldots +I_0R^{n-1}\approx I_0\times(1-R^n)/(1-R)$. Here R is the reflection coefficient of the inner mirror surface, which determines the photon absorption loss by the walls in each reflected generation before they leave the chamber at the n-pass (for an average photon). In turn, for a cylindrical chamber with an internal diameter of 6 cm and a length of no more than 9 cm, the surface area of the irradiation chamber in the computational model will be $2\pi d^2/4+\pi dL\approx 225$ $cm^2$, the volume of $\pi d^2$ $L/4\approx 250$ $cm^3$. Thus, according to the previously obtained similarity formula (a), the parameter $E_\nu\approx E_\nu$ $(V_0)/|1n(V/V_0)|\approx 300/|1n(400/250)|\approx 640$ $\mu J/cm^3$. It should be noted that the above chamber parameters (in the example of using the claimed inactivation device as part of the RPE) are given for clarity of calculation for reasons of ergonomics, ease of operation, maintenance and engineering considerations.

With reference to FIG. 1. the inactivation device consists of a housing (1) with side walls and end walls (2), a UV LED (3), a UV reflective coating of the walls (4) and air-conducting slits/holes (5) in the end walls. FIG. 1. shows, in essence, a version of the cylindrical shape device, the most technologically feasible in terms of practical manufacturing. However, for a specialist, it is obvious that the specific form of the device chamber in terms of performance and achieving the desired result is optional, and is determined essentially by the technical and technological capabilities of a particular production.

The possibility of UV radiation reflection by the inner surface of the inactivation chamber walls in practical variants can be realized, for example, by using various coatings applied or glued to the inner surface of the walls—specially treated $MgF_2$ or other suitable reagent of aluminum foil, thin metal sheets, silver or gold films, etc. Selective examples of coatings based on [6] are presented in the following table 1.

TABLE 1

| Name, dimensions | Features and characteristics | Price |
|---|---|---|
| Reflective aluminum mirror sheet, class A 1000 * 120 * 0.4 mm | ~95% reflectivity, 9% diffuse reflectivity | 65 c.u./sheet |
| Reflective aluminum mirror sheet, class A+ 1000 * 100 * 0.4 mm | ~99% reflectivity, 3% diffuse reflectivity (supermirror) | 100 c.u./sheet |
| Reflective aluminum mirror sheet, class A 500 * 120 * 0.4 mm | ~95% reflectivity, 9% diffuse reflectivity | 40 c.u./sheet |

TABLE 1-continued

| Name, dimensions | Features and characteristics | Price |
|---|---|---|
| Reflective aluminum mirror sheet, class A 500 * 100 * 0.4 mm | ~95% reflectivity, 9% diffuse reflectivity | 35 c.u./sheet |
| Reflective aluminum mirror sheet, class B 1000 * 120 * 0.8 mm | ~90% reflectivity, 10% diffuse reflectivity | 135 c.u./sheet |

Table 1 clearly shows that it is industrially feasible to use UV reflectors with a reflection coefficient of up to 99%.

As an example of using an LED with an ultraviolet radiation spectrum with reference to [8], we can mention the LED G6060 of the LEUVA66H70HF00 series with a wavelength of 278 (270-285) nm, radiation power of 70-110 mW, 6.5 V, 350-500 mA, dimensions 6.0×6.0×1.35 mm.

It is obvious to a specialist that it is also possible to use a combination of LEDs in the form of a group of diodes on one or different boards, including the possibility of locating (fixing) such LEDs at various points in the internal volume of the irradiation chamber. For a similar implementation, for example, refer to the SMD 3535 LED model JZ-UFDC3535FFQUSC-RO with a wavelength of 275 (265-285) nm, current 100-150 mA, 6 V, radiation power 12 MW, dimensions 3.6×3.6×1.62 mm, [9].

The possibility of practical implementation of the claimed inactivation device within the framework of the RPE will be considered with reference to FIG. 2, where the following positions are indicated by numbers: the RPE mask—6; UV-LED power supply—7; a removable external filter—8; an air-permeable screen—9. Structurally, the inactivation device as part of the RPE can be designed, for example, as an attachment to the respiratory part of the device-respirator in the area of the nasolabial triangle. The inactivation device can also be made in the form of a replaceable cartridge installed in an attachment located on the mask (housing) of the RPE. The inhaled air enters through an external filter (8) to an air slit, located by analogy with a flange, to reduce radiation losses during scattering and reflection from the volume of the irradiation chamber. A similar circular slit serves for the entry of irradiated air into the respiratory organs. When exhaling, the flow goes in the opposite direction through the same chamber, i.e. both inhaled and exhaled air is disinfected with almost the same efficiency.

An RPE with an inactivation device can also be designed with a visor and two valves behind the inlet filter for inhalation and for exhalation—a separate duct with the exit of disinfected air from the irradiation chamber in the upward direction under the transparent visor. In this version, the constant inflow of UV-treated exhaled air under the visor creates a protective layer (increased pressure of the decelerating flow) for the mucous membranes of eyes in conditions of a leaky cover. The visor itself serves as a barrier to the direct ingress of the infected aerosol into the eyes, as well as a means of forming a protective layer of irradiated exhaled air with increased pressure. It is also possible to use a full facepiece respirator with a plastic or glass transparent window (filter analogues: STALKER-25, 3M 6900 filter 6057, etc.) and an air supply through a respiratory type device (as described above) or through a top nozzle with a vertical irradiation chamber, similar to swimming masks. The latest modification with a vertical nozzle can be equipped with a multi-pass irradiation chamber of a larger size, an exhalation valve and a boost fan to increase comfort during prolonged wearing of the device.

The question of choosing the dimensions of the slits/holes in the ends of the inactivation device, on the one hand, lies in practical field from the condition of ensuring the comfort of breathing, and, on the other hand, ensuring the presence of photons in the internal volume of the chamber. From the data published in [7], it follows that the average air consumption by human lungs, depending on physical activity and emotional state, is within the range of the flow rate per second for inhalation and exhalation v—500-2000 $cm^3/s$. Based on this data, to calculate the maximum air flow through the irradiation chamber during human breathing (the dimensions of the slits/holes), it is possible to be guided by the average experimental data on pulmonary ventilation, the true amount of oxygen consumption and heat generation of an adult according to Table 2.

TABLE 2

| State of rest and characteristics of the activity performed | The intensity of external activity kgf * m/min | Pulmonary ventilation 1/min | True oxygen consumption 1 (n)/min | Heat production kcal/min |
|---|---|---|---|---|
| Rest | — | 5-6 | 0.25-0.3 | 1.25-1.5 |
| Very light activity | — | 6-10 | 0.3-0.5 | 1.5-2.5 |
| Light activity | — | 10-16 | 0.5-0.8 | 2.5-4.0 |
| Moderate activity | 250-450 | 16-25 | 0.8-1.2 | 4.0-6.0 |
| Vigorous activity | 450-800 | 25-40 | 1.2-2.0 | 6.0-10.0 |
| Hard activity | 800-900 | 40-50 | 2.0-2.5 | 10.0-12.5 |
| Very hard activity | 900-1250 | 50-60 | 2.5-3.0 | 12.5-15.0 |
| Maximum effort activity | More than 1250 | More than 60 | More than 3.0 | More than 15.0 |

For example, by analogy with respirators equipped with removable dust filters, for the comfort of breathing, we will choose the air intake slit area twice as large, since in this case there are two slits, and therefore two hydraulic resistances. The standard respirator has an air inlet/outlet area of about 3 $cm^2$. Thus, this device has two slits of 6 $cm^2$ each. The total area of possible radiation loss (leakage) is about 12 $cm^2$. This allows us to estimate the average number of photon passes before leaving the multi-pass chamber as the ratio of the entire reflecting surface area to the leakage holes area. Therefore, n~225/12≠18-19 reflections (passes through the chamber).

Let us determine the increase in the (flux) intensity of the optical field due to the multi-pass reflective system in the irradiation chamber: $I/I_0$ for reflection coefficients R=0.95 and 0.99. For 0.95, the increase will be about 12, and for 0.99, about 16.5. The difference is not very significant. In further calculations, we will take this coefficient in the amount of 15. Thus, according to inhaled air consumption, the power of the optical field in the chamber is: $W_\lambda = E_v \times v \approx 0.3\text{-}1.2$ W, hence the required power of the emitter for the RPE (mask) is 20-80 mW.

Practical variant of application of the claimed inactivation device can also be a small-sized air recirculating UV device with low energy consumption, with high technological and price availability for use in transport (subway and passenger railroad cars, bus and minibus cabins, water and air transport cabins and salons, personal vehicles, military and special equipment). The circuit diagram of the device is shown in FIG. 4, where the following positions are indicated by numbers: 10—electric motor; 11—fan; 12—air intake bell mouth; 13—air exhaust bell mouth; 14—radiation shield; 15—removable filter; 16—support stands. As in the case of the RPE, the device is based on the inactivation device FIG. 1. with a multi-pass UV irradiation chamber of the air flow.

This device is designed for a constant rather high air flow, with forced circulation by using a fan and an electric motor. Air flow is calculated on the basis of an acceptable time to disinfect the air in a given empty room (volume) in an acceptable time; and also on the basis of people in the room, subject to the rhythm of their breathing, depending on the type of their activity and on the condition that this device will inactivate per unit of time at least as many virions of a certain type as all those present could emit if they were infected. To optimize the operation of the device, it can be implemented a multi-level operating mode with several air pumping rates and several UV sources in the irradiation chamber. The principle of the irradiation chamber organization does not differ from the previous device of the RPE. This is a multi-pass optical resonator with slotted holes along the flanges for pumping air.

As an example of such a device with reference to FIG. 4. it is proposed to use of a group of 3 UVC LEDs full power of 1 W each—UVC G6060 with medium wave 260-275 nm (power consumption of 1-3 W, light power of about 70-110 mW, price from the manufacturer 70-90 $) [8]. In the air pumping mode of 20 liters/sec. (equivalent to calm breathing of 40 people) provides inactivation of up to 99.0% of virions with double-stranded DNA or guaranteed 99.9% of virions such as COVID-19 for irradiation chamber dimensions d=10 cm/L=30 cm.

The device consumes about 20-25 W of electricity. The main part of it is accounted for by the fan (about 60-70%). The device can operate from on-board (6, 12, 24 V) or general electrical network with an adapter, on-board battery or own autonomous power source. As an example, the same bactericidal efficacy would require 5-7 W of lamp recirculators light power without a multi-pass irradiation chamber (calculation according to [5]), and energy consumption would be about 100 W (~70% to power the emitters). The weight and dimensions of such a device would be significantly greater.

Figure 6:
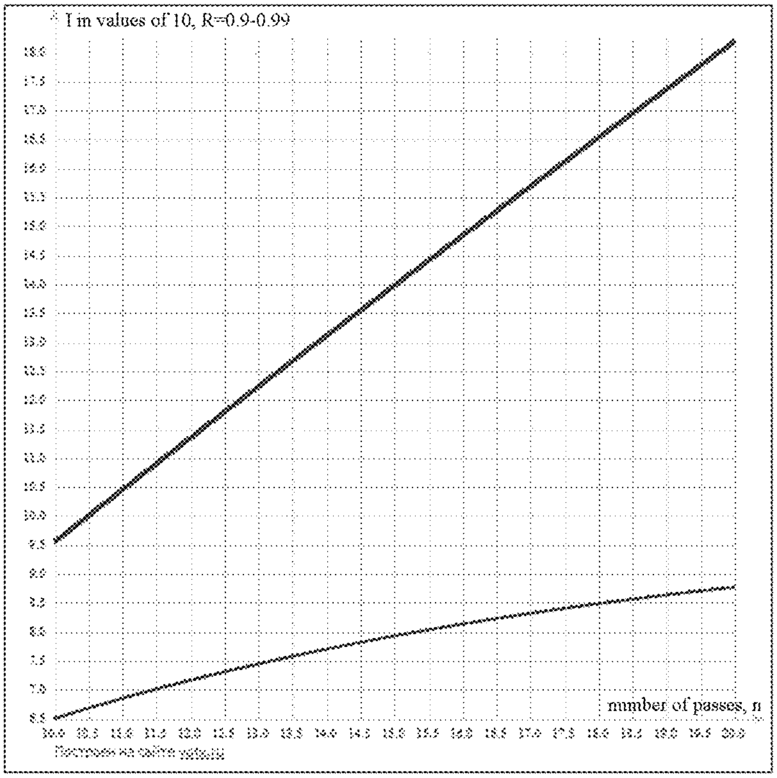

The bactericidal efficacy increase of the claimed group of inventions due to application of multi-pass optical air flow irradiation chamber and, as a consequence, increase of optical field intensity is clearly illustrated by graphs of optical field intensity depending on reflection coefficient and average number of reflections (passes) in FIG. 5 and FIG. 6. It can be seen from the presented graphs that, based on the computational and experimental model, the application of the claimed technical solution, namely, the arrangement of a separate multi-pass optical irradiation chamber in an RPE or a mobile air recirculator with UV irradiation on UVC-emitting diodes, can reduce the power of primary sources required to achieve the desired inactivation parameters by more than an order of magnitude. It is obvious that the energy consumption of devices and parasitic heat generation, as well as their cost, are reduced in the same proportion, which makes their production and operation technically feasible and economically attractive.

The invention claimed is:

1. A device configured to inactivate pathogenic microorganisms in an air flow, the device comprising;

a flow-through chamber having an internal volume, one or more walls limiting the internal volume;

at least one LED configured to emit light in the ultraviolet radiation spectrum located in the internal volume of the chamber, an entire internal surface of at least one of the one or more walls being coated with or made of a material that reflects ultraviolet radiation and forms a multi-pass optical system that, based on the material and the internal volume's geometry, provides a photon flux (number of units emitted per unit of time) increased relative to that provided by the at least one LED and approximately equal to $I_0\times(1-R^{11})/(1-R)$; and at least first and second through-slits or holes -made in at least one of the of the one or more walls, the first through-slit or hole being an inlet, the second through-slit or hole being an outlet for the air flow flowing through the internal volume of the chamber, where $I_0$ is the initial photon flux from the at least one LED, R is the reflection coefficient of the material, and n is the average number of reflections provided by the material before the photons are lost through the at least first and second through-slits or holes.

2. The device of claim 1, further comprising an LED power supply.

3. The device of claim 1, wherein the chamber is made of cylindrical, spherical, hemispherical, simple or complex geometric shape with intersecting curved surfaces.

4. The device of claim 1, wherein the ratio of the sum of all slits or holes areas to the entire area of the inner surface of, at least, one specified chamber wall is minimal based on air flow passage during inhalation/exhalation or air pumping.

5. The device of claim 1, wherein the chamber is cylindrical with an internal diameter of 6-9 cm.

6. The device of claim 1, wherein the material reflects at least 90% of UV radiation with less than or equal to 10% diffuse reflectivity.

7. The device of claim 1, wherein the material reflects at least 95% of UV radiation.

8. The device of claim 1, wherein the at least one LED comprises a plurality of LEDs located at different respective locations inside the chamber.

9. The device of claim 1, wherein the multi-pass optical system is configured to support up to 19 reflections inside the chamber prior to photon loss through the at least first and/or second through-slits or holes.

10. The device of claim 9, wherein the material is selected to facilitate an increase in the flux of the ultraviolet radiation optical field produced by the at least one LED by at least a factor of 12.

11. The device of claim 1, wherein the material is selected to facilitate an increase in the flux of the ultraviolet radiation optical field produced by the at least one LED by at least a factor of 12.

12. The device of claim 1, wherein the at least first and second through-slits or holes are sized, and the material is selected, to facilitate 18-19 reflections of ultraviolet radiation from the at least one LED prior to photon loss through the at least first and/or second through-slits or holes.

13. The device of claim 12, wherein the material is selected to facilitate an increase in the flux of the ultraviolet radiation optical field produced by the at least one LED by a factor of 12-16.5.

14. An air disinfection device containing an air intake and forced air pump, an exhaust bell mouth, and the device of claim 1, the first through-slit or hole facing the air intake and forced air pump, and the second through-slit or hole facing the exhaust bell mouth.

15. A personal respiratory protection device comprising a mask configured to cover at least the respiratory organs, with at least one airway and an attachment mounted on the mask, which is made from or contains the device of claim 4, such that the second through-slit or hole faces the at least one airway, and the first through-slit or hole faces the surrounding atmosphere and is covered by a breathable filter.

16. The device of claim 15, wherein an air-permeable membrane or filter is additionally located between the mask and the second through-slit or hole.

17. The device of claim 15, wherein the first through-slit or hole is additionally closed by a breathing valve.

* * * * *